(12) United States Patent
Revellame et al.

(10) Patent No.: US 11,547,654 B2
(45) Date of Patent: Jan. 10, 2023

(54) METHOD OF MANUFACTURE FOR HAND-SANITIZING LOTION WITH PROLONGED EFFECTIVENESS AND RESULTING COMPOSITION OF MATTER

(71) Applicant: University of Louisiana at Lafayette, Lafayette, LA (US)

(72) Inventors: Emmanuel D. Revellame, Lafayette, LA (US); William E. Holmes, Lafayette, LA (US)

(73) Assignee: University of Louisiana at Lafayette, Lafayette, LA (US)

(*) Notice: Subject to any disclaimer, the term of this patent is extended or adjusted under 35 U.S.C. 154(b) by 0 days.

(21) Appl. No.: 16/114,651

(22) Filed: Aug. 28, 2018

(65) Prior Publication Data
US 2019/0060213 A1    Feb. 28, 2019

Related U.S. Application Data

(60) Provisional application No. 62/550,801, filed on Aug. 28, 2017.

(51) Int. Cl.
| | |
|---|---|
| *A61K 8/92* | (2006.01) |
| *A61K 8/41* | (2006.01) |
| *A61K 8/73* | (2006.01) |
| *A61K 8/31* | (2006.01) |
| *A61K 8/55* | (2006.01) |
| *A61K 8/67* | (2006.01) |

(Continued)

(52) U.S. Cl.
CPC .............. *A61K 8/922* (2013.01); *A01N 33/12* (2013.01); *A61K 8/31* (2013.01); *A61K 8/416* (2013.01); *A61K 8/55* (2013.01); *A61K 8/678* (2013.01); *A61K 8/73* (2013.01); *A61K 8/732* (2013.01); *A61Q 17/005* (2013.01); *A61Q 19/10* (2013.01); *A61K 2800/48* (2013.01); *A61K 2800/524* (2013.01); *A61K 2800/805* (2013.01)

(58) Field of Classification Search
CPC ...... A61Q 19/10; A61Q 17/005; A01N 33/12; A61K 8/922; A61K 8/416; A61K 8/732; A61K 8/31; A61K 8/55; A61K 8/678; A61K 8/73; A61K 2800/48; A61K 2800/524; A61K 2800/805
See application file for complete search history.

(56) References Cited

U.S. PATENT DOCUMENTS

| | | | | |
|---|---|---|---|---|
| 4,929,439 A | * | 5/1990 | Cotteret | A61K 8/466 424/59 |
| 5,661,119 A | * | 8/1997 | Hersh | A61K 8/9794 510/139 |

(Continued)

FOREIGN PATENT DOCUMENTS

| | | |
|---|---|---|
| CN | 1938009 A | 3/2007 |
| WO | 9949878 A1 | 10/1999 |

*Primary Examiner* — Hong Yu
(74) *Attorney, Agent, or Firm* — Kean Miller LLP; Russel O. Primeaux; Lauren J. Rucinski

(57) ABSTRACT

This invention is a novel method of manufacture for hand-sanitizing lotions that retains the added benefits of prolonged effectiveness while avoiding demulsification as well as the resulting product. The invention presents a novel, more simplified process comprising a lower cooking temperature and an optimized ingredient addition protocol, designed for product stability and ingredient integrity.

13 Claims, 3 Drawing Sheets

(51) Int. Cl.
*A61Q 17/00* (2006.01)
*A01N 33/12* (2006.01)
*A61Q 19/10* (2006.01)

(56) References Cited

U.S. PATENT DOCUMENTS

| | | | | |
|---|---|---|---|---|
| 5,676,994 | A | * | 10/1997 | Eskins ............... A21D 2/16 426/602 |
| 5,792,793 | A | * | 8/1998 | Oda ................. A01N 31/02 106/1.05 |
| 5,871,756 | A | | 2/1999 | Jeffcoat et al. |
| 6,015,832 | A | * | 1/2000 | Baker, Jr. ............ A01N 25/04 514/546 |
| 6,113,887 | A | | 9/2000 | Mori et al. |
| 6,518,307 | B2 | | 2/2003 | McKenzie et al. |
| 6,660,776 | B1 | | 12/2003 | McDaniels, III et al. |
| 2001/0006680 | A1 | * | 7/2001 | Mansouri ............ A61K 8/24 424/499 |
| 2003/0103914 | A1 | | 6/2003 | Lawlor |
| 2005/0100621 | A1 | * | 5/2005 | Popp ................. A61K 8/42 424/776 |
| 2005/0192197 | A1 | * | 9/2005 | Man ................. A61K 31/327 510/375 |
| 2009/0062389 | A1 | | 3/2009 | Patel et al. |
| 2009/0226498 | A1 | * | 9/2009 | Flugge-Berendes .... A61P 17/16 424/411 |

\* cited by examiner

FIGURE 1

| Materials/Ingredients | Function | Concentration (wt. %) |
|---|---|---|
| 1. Benzalkonium Chloride (BKC) | Active* | 0.13 ±0.01 |
| 2. Tri-n-Butyl Phosphate (TnBP) | Anti-foam | 0.15 ±0.01 |
| 3. Methyl Paraben (MP) | Preservative | 0.10 ±0.005 |
| 4. Propyl Paraben (PP) | Preservative | 0.10 ±0.005 |
| 5. Citricidal (Cc) | Antioxidant | 0.15 ±0.015 |
| 6. d-α-Tocopherol Acetate (daTA) | Vitamin E | 0.06 ±0.003 |
| 7. Waxy Corn Starch (WCS) | Emulsifier | 6.33 ±0.20 |
| 8. Xanthan (Xt) | Thickener | 0.38 ±0.020 |
| 9. Pectin (Pt) | Thickener | 0.76 ±0.020 |
| 10. Soy Bean Oil (SBO) | Oil-phase | 1.69 ±0.060 |
| 11. Petrolatum (Pl) | Skin protectant | 0.84 ±0.040 |
| 12. Deionized Water (DW) | Water-phase | balance |

*Main Active Ingredient

METHOD OF MANUFACTURE FOR HAND-SANITIZING LOTION WITH PROLONGED EFFECTIVENESS AND RESULTING COMPOSITION OF MATTER

CROSS REFERENCE TO RELATED APPLICATIONS

This application claims priority to U.S. Provisional Application No. 62/550,801 entitled "METHOD OF MANUFACTURE FOR HAND-SANITIZING LOTION WITH PROLONGED EFFECTIVENESS" filed Aug. 28, 2017.

STATEMENT REGARDING FEDERALLY SPONSORED RESEARCH OR DEVELOPMENT

Not applicable.

REFERENCE TO A "SEQUENCE LISTING," A TABLE, OR A COMPUTER PROGRAM

Not applicable.

DESCRIPTION OF THE DRAWINGS

The drawings constitute a part of this specification and include exemplary embodiments of the Method of Manufacture for Hand-Sanitizing Lotion with Prolonged Effectiveness, which may be embodied in various forms.

FIG. 1 is table that includes the function and concentration of materials comprising the hand-sanitizing lotion with prolonged effectiveness.

BACKGROUND

Figure 2A:
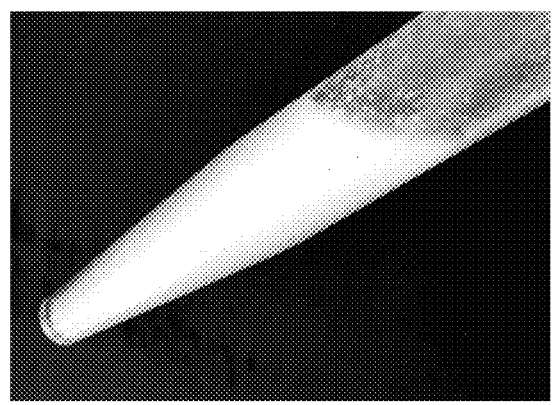
FIG. 2(a) is a depiction of the hand-sanitizing lotion with prolonged effectiveness.
Figure 2:
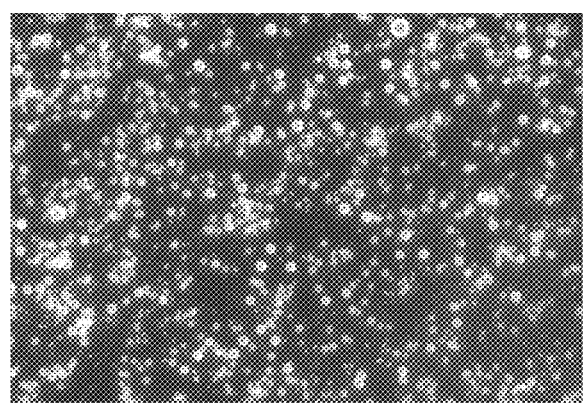
FIG. 2(b) is a microscopic view of the hand-sanitizing lotion with prolonged effectiveness.

The subject matter of the present invention is described with specificity herein to meet statutory requirements. However, the description itself is not intended to necessarily limit the scope of claims. Rather, the claimed subject matter might be embodied in other ways to include different steps or combinations of steps similar to the ones described in this document, in conjunction with other present or future technologies.

Furthermore, the described features, structures, or characteristics may be combined in any suitable manner in one or more embodiments. In the following description, numerous specific details are provided, such as examples of ingredients, heating mechanisms, and mixing times. One skilled in the relevant art will recognize, however, that the Method of Manufacture for Hand-Sanitizing Lotion with Prolonged Effectiveness may be practiced without one or more of the specific details, or with other methods, components, materials, and so forth. In other instances, well-known structures, materials, or operations are not shown or described in detail to avoid obscuring aspects of the invention.

Most hand sanitizers commonly used in the marketplace are alcohol-based, which are effective against common pathogens. However, the effectiveness of these sanitizers drastically diminishes as the alcohol evaporates from the skin after application. Thus, users who are continuously at risk of being exposed to microbes (e.g. healthcare professionals, bank tellers, daycare workers, etc.) need to apply alcohol-based sanitizers frequently for continuous protection. Extended exposure to alcohol often results in skin irritation, dryness, enlarged pores, and other undesirable side effects which also make the skin more susceptible to infection. Therefore, a more ideal hand-sanitizer is needed that provides prolonged effectiveness while avoiding damage to the user's skin. A hand-sanitizer with these properties will lessen application frequency and help maintain the healthiness of the skin.

Skin lotions provide a suitable carrier for anti-microbial agents and do not irritate the skin like alcohol-based sanitizers. Rather, skin lotions provide enhanced benefits to skin's texture and over-all health and provide a more controlled release, prolonging effectiveness of the sanitizer. Generally, skin lotions are a type of oil-in-water emulsion, wherein the oil is the dispersed phase, and water is the dispersion medium. Emulsions contain both a dispersed and a continuous phase, with the boundary between the phases called the "interface." In the case of typical skin lotions, the oil is the dispersed phase and the water is the continuous phase.

Skin lotions are typically microemulsions which are a special class of emulsions with droplet sizes below a certain level which cause them to appear translucent. Common emulsions are inherently unstable and over time, emulsions tend to revert to the stable state of the phases comprising the emulsion, e.g., the ingredients separate or settle. Previous lotion based sanitizers suffer from this emulsion destabilization or demulsification. This is due to manufacturing protocols that are not optimized with respect to temperature, shearing, water content, and the order of addition of the ingredients.

The current invention is a novel method of manufacture for hand-sanitizing lotions that retains the added benefits of prolonged effectiveness while avoiding the demulsification described above. As opposed to prior work, a more simplified process consisting of fewer steps is involved in the invention. The invention also involves lower cooking temperature and an optimized ingredient addition protocol designed for product stability and ingredient integrity.

DETAILED DESCRIPTION

This invention is directed to a novel method of manufacturing a unique formula of ingredients which moisturizes the skin while at the same time acts as sanitizer ("the product"). The product is a microemulsion that contains three main components: a water-based component, an oil-based component, and an emulsifier. When these three components are mixed in a certain proportion (with the aid of the other components), a stable microemulsion is formed. Many factors dictate whether or not the emulsification process will be successful including: temperatures, shearing forces, and water content. These factors could also vary based on the additional ingredients added to the emulsion. Therefore, the order of the addition of the ingredients is critical to exposing the right ingredients to the right process factors described above so that all ingredients retain their functionality on a stable product.

One embodiment of the components involved in the manufacture of the product, along with their functions is listed in Table 1. An anti-microbial agent ("an active") that is oil-miscible provides a suitable component of the sanitizer. Alternatively, an active that will remain at the emulsion interface (i.e. surfactants) would also be suitable. In addition to oil-miscible or interface-retained actives, water-miscible actives may also be added during formulation. In this embodiment, the main active ingredient is benzalkonium chloride ("BKC"). BKC is a cationic surfactant that is commonly found in pharmaceutical (e.g. contact lens solutions, eye and nasal solutions and medications, skin cleansers, skin creams and medications, lozenges, medications for mouth and throat, etc.) as well as personal care products (e.g. cosmetics, shampoos, deodorants, mouthwash, etc.). As a lotion, the product contains Vitamin E and petrolatum for skin protection. The rest of the ingredients are added for the purpose of producing a stable microemulsion as product.

Figure 3:
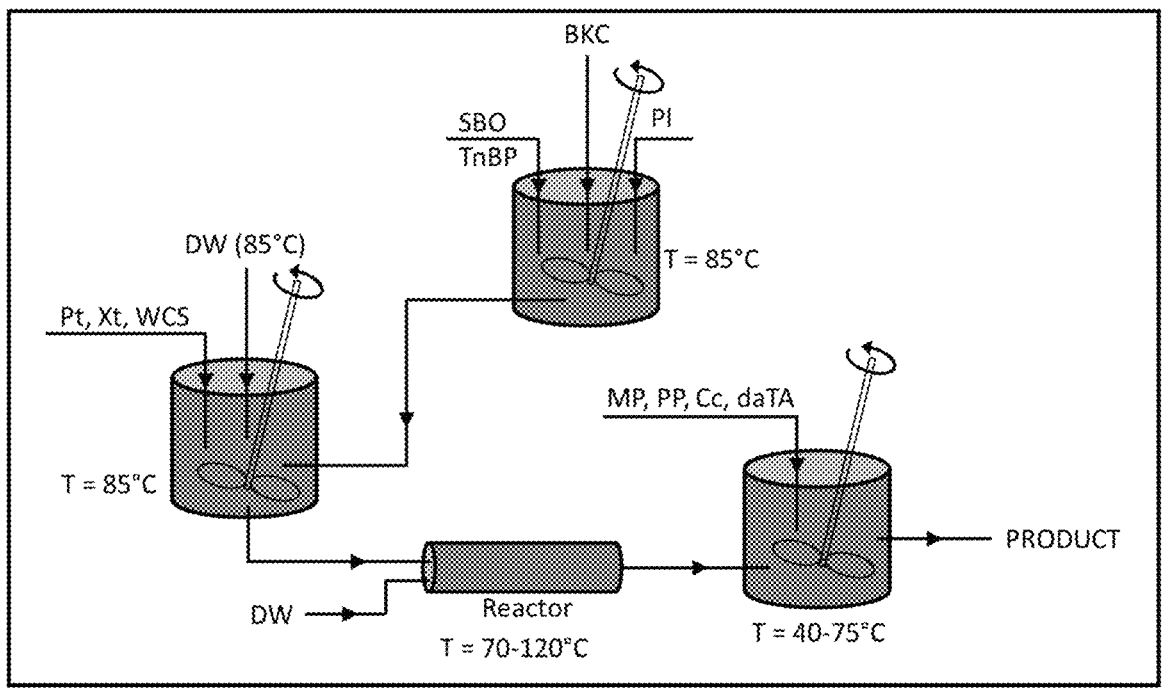
FIG. 3 is a graphical depiction of the manufacturing process of the invention.

The process flowchart of one embodiment of the invention is presented in FIG. 3. In the first step of the depicted embodiment, the deionized water is heated in a vessel to a temperature of 85° C. Waxy cornstarch, pectin, and xanthan are added to the vessel once the water reaches the desired temperature. The mixture is then blended until it is devoid of lumps and concentrated amounts of solid. A typical blending time is 20 minutes; however, other blending times may be suitable.

In a separate vessel, soybean oil is heated to a temperature of 85° C. BKC, petrolatum, and tri-n-butyl phosphate are added to this separate vessel once the soybean oil reaches the desired temperature. The soybean oil-BKC-petrolatum-tri-n-butyl phosphate mixture is blended until it becomes mostly clear and homogeneous throughout visually. A typical blending time is 10 minutes; however other blending times may be suitable.

The soybean oil-BKC-petrolatum-tri-n-butyl phosphate mixture is then slowly incorporated into the water-cornstarch-pectin-xanthan mixture. The incorporation method should be performed under high shear/agitation conditions. After incorporation, the resulting mixture is stirred for at least 30 minutes and then passed through a heating means. Suitable heating means include any heated batch or continuous stirred reactor capable of operating at temperatures between 70° C. and 120° C. A suitable material for the reactor includes stainless steel. In one embodiment, the heating mechanism is a jet cooking apparatus that injects steam directly to the reactor with steam pressures of 60-100 psi. In another embodiment, the steam pressure is 70 psi. In other embodiments, a microwave heating system is used in conjunction with the direct-steam injection in order to heat the reactor. In yet another embodiment, the heating means comprises a microwave heating system with a 915 MHz (up to 100 kW) power generator, power coupler, and focusing cavity. The contents of the reactor may be agitated through steam injection and chaos mixing. In one embodiment, the steam used in the agitation step is injected at a rate of 550 lbs per hour. Any suitable chaos mixer means may be used. In one embodiment, an in-line 4" chaos mixer equipped with a 7.5 HP centrifugal pump is used.

In the final mixing step of the depicted embodiment, preservatives and a skin soothing agent are successively added to the resulting mixture. In one embodiment, the preservatives are propyl paraben, methyl paraben and citricidal. In one embodiment, the skin soothing agent is Vitamin E in the form of d-α-tocopherol acetate. Vitamin E which is a heat labile substance is added after cooking to ensure that the product contains unaltered form of Vitamin E.

Finally, after all of the remaining ingredients are combined into the resulting mixture, the mixture is stirred for an additional 10 minutes. The viscosity of the mixture is then determined. Based on the viscosity measurement, variable amounts of water are added to the mixture and additional 10 minutes of stirring, if so required. The desired viscosity is between 3,250 and 3,750 cP. Once the viscosity is confirmed, the pH is checked and adjusted accordingly using HCl or NaOH solutions. The desired pH is between 3.9 and 4.1.

In one embodiment, the hand-sanitizing lotion with prolonged effectiveness is capable of destroying the yeast, *Candida auris*. One skilled in the art would recognize that the invention may be used for destroying or limiting the effects of many fungals and/or microbials. In this specific embodiment, a test article was inoculated with *Candida auris*. The concentration of the microorganism was determined after 40 seconds, 15 minutes, and after 4 hours of incubation at 24° C. The removal of the yeast after 15 min was 93-99%, after 30 min to 4 hours >99.3% yeast cells died.

A slant with yeast growth, mailed by the culture collection, was used to inoculate several Petri dishes containing the DPY agar. The plates were inoculated for 7 days at 24° C. to verify the culture purity. A second transfer of an individual yeast colony to fresh DPY plates was made and the plates were again inoculated for 7 days at 24° C. This guarantees the purity of the yeast culture. The yeast growth from the second passage was collected with a microbiological loop and suspended in either sterile de-ionized water or sterile physiological solution. Both preserve the viability of *C. auris* cells equally well.

Two hundred microliters of *C. auris* suspension ($6.8 \times 10^6$ viable cells per ml) was mixed with 4.8 ml of the invention in test tubes and incubated at 22° C. Aliquots were taken after 40 sec., 15 min and 4 hours. The 15 min incubation experiment was conducted twice, since this incubation time was considered a reasonable working time for most hospital/household applications. In a separate experiment, an additional 0.2 ml aliquot of the *C. auris* suspension was added after 15 min of incubation and the incubation was continued for another 15 min, thus totaling 30 min. This was done to assess the effectiveness of the test article against additional *C. auris* pathogens after its application. In a control experiment, 4.8 ml of sterile de-ionized water were added instead of the lotion. The control was incubated for the same time as the invention test tubes and aliquoted after 15 min. and 4 hours.

The aliquots were serially diluted in de-ionized water (−2, −4, −6) immediately after their withdrawal from the incubation tubes and 0.1 ml of each dilution was plated in triplicates on the DPY agar. Colonies were counted following 7 day incubation at 24° C. The killing of the C. auris culture was calculated as a percentage of colonies which grew on the DPY agar following incubation with the invention and colonies which grew on the DPY agar following incubation in de-ionized water. The results are presented in Table 2 below:

|  | Incubation Time | | | |
| --- | --- | --- | --- | --- |
|  | 40 sec | 15 min | 30 min | 4 hours |
| Run 1 | 79% | 93% | 99.3% | 99.3% |
| Run 2 |  | 99% |  |  |

The results of the example show that the invention is an effective killing agent of *C. auris*, provided that the lotion remains in a contact with the skin/surface containing the pathogen for longer than 15 minutes.

For the purpose of understanding the Method of Manufacture of Hand-Sanitizing Lotion with Prolonged Effectiveness, references are made in the text to exemplary embodiments of a Method of Manufacture of Hand-Sanitizing Lotion with Prolonged Effectiveness, only some of which are described herein. It should be understood that no limitations on the scope of the invention are intended by describing these exemplary embodiments. One of ordinary skill in the art will readily appreciate that alternate but functionally equivalent components, materials, designs, and equipment may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

Reference throughout this specification to features, advantages, or similar language does not imply that all of the features and advantages that may be realized should be or are in any single embodiment. Rather, language referring to the features and advantages is understood to mean that a specific feature, advantage, or characteristic described in connection with an embodiment is included in at least one embodiment. Thus, discussion of the features and advantages, and similar language, throughout this specification may, but do not necessarily, refer to the same embodiment.

Furthermore, reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change to the basic function to which it is related.

The invention claimed is:

1. A method of manufacturing hand-sanitizing lotion comprising:
   a. heating deionized water in a vessel;
   b. mixing a waxy corn starch and at least one thickener to said deionized water and blending said deionized water, at least one thickener, and waxy corn starch to create a first mixture;
   c. heating soybean oil in a second vessel;
   d. adding at least one active ingredient, a skin protectant and an anti-foam agent to said heated soybean oil and blending said heated soybean oil, said at least one active ingredient, said skin protectant, and said anti-foam agent to create a second mixture, wherein said at least one active ingredient comprises benzalkonium chloride;
   e. blending said second mixture and said first mixture;
   f. gelatinizing and emulsifying the resulting mixture simultaneously by passing said resulting mixture through an agitation and heating means selected from the group consisting of: chaos mixing and steam injection;
   g. successively adding a preservative, at least one antibacterial agent, and at least one skin soothing agent to said resulting mixture to create and blend a final mixture; and
   h. cool said final mixture until it reaches room temperature.

2. The method of claim 1 wherein said thickener is chosen from the group comprising pectin and xanthan.

3. The method of claim 1 wherein said deionized water is heated at a temperature of 85° C.

4. The method of claim 1 wherein said blending of said heated water, at least one thickener, and at least one emulsifier is performed for 10 to 30 minutes.

5. The method of claim 1 wherein said at least one active ingredient is a surfactant.

6. The method of claim 1 wherein said skin protectant comprises petrolatum.

7. The method of claim 1 wherein said anti-foam agent comprises Tri-n-Butyl Phosphate.

8. The method of claim 1 wherein said heating means is capable of reaching temperatures between 70 and 120° C.

9. The method of claim 1 wherein said heating means comprises a jet cooking apparatus.

10. The method of claim 1 wherein said successively adding step further comprises adding each of said preservative, said at least one antibacterial agents, and said at least one skin soothing agent successively over at least 30 minutes.

11. The method of claim 1 wherein said successively adding step further comprises cooling while blending said resulting mixture until the viscosity of said final mixture is between 3250 and 3750 cP.

12. The method of claim 1 further comprising the step of adjusting the pH of said final mixture until the pH of said final mixture is between 3.9 and 4.1.

13. A method of manufacturing hand-sanitizing microemulsion mixture comprising:
   a. heating deionized water in a vessel to a temperature of 85 degrees Celsius;
   b. adding waxy cornstarch at 6.33±0.020 wt. % of the microemulsion mixture, pectin at 0.76±0.020 wt. % of the microemulsion mixture, and xanthan at 0.38±0.020 wt. % of the microemulsion mixture to said vessel to form a first vessel mixture;
   c. blending said first vessel mixture until said contents are devoid of lumps and concentrated amounts of solid;
   d. heating soybean oil at 1.69±0.060 wt. % of the microemulsion mixture in a second vessel to a temperature of 85 degrees Celsius;
   e. adding benzalkonium chloride at 0.10-0.13 wt. % of the microemulsion mixture, petrolatum at 0.84±0.040 wt. % of the microemulsion mixture, and tri-n-butyl phosphate at 0.15±0.01 wt. % of the microemulsion mixture to said second vessel to form a second vessel mixture;
   f. blending said second vessel mixture until it becomes homogeneous;
   g. blending and incorporating said second vessel mixture into said first vessel mixture under high shearing and high heating conditions resulting in a gelatinized and emulsified blended mixture;
   h. stirring said blended mixture while successively adding at least one preservative selected from the group consisting of methyl paraben at 0.10±0.005 wt. % of the microemulsion mixture, propyl paraben at 0.10±0.005 wt. % of the microemulsion mixture, and d-α-tocopherol acetate at 0.06±0.003 wt. % of the microemulsion mixture to said blended mixture resulting in the microemulsion mixture;

i. cooling said microemulsion mixture to room temperature while stirring the microemulsion mixture until the viscosity measurement is between 3,250 and 3,750 cP; and j. adjusting the pH of the microemulsion mixture by adding at least one selected from the group consisting of hydrochloric acid and sodium hydroxide until the pH of the microemulsion mixture is between 3.9 and 4.1.

* * * * *